United States Patent [19]

Nozaki et al.

[11] Patent Number: 5,300,653

[45] Date of Patent: Apr. 5, 1994

[54] SEPARATION METHOD OF AMINO ACIDS

[75] Inventors: Shohei Nozaki, Yokohama; Naohiro Murata, Kamakura; Kiyoo Miyazaki, Yotsukaido, all of Japan

[73] Assignee: Mitsui Toatsu Chemicals, Incorporated, Tokyo, Japan

[21] Appl. No.: 995,959

[22] Filed: Dec. 23, 1992

Related U.S. Application Data

[63] Continuation of Ser. No. 612,478, Nov. 14, 1990, abandoned.

[30] Foreign Application Priority Data

Nov. 20, 1989 [JP]   Japan ................................... 1-299500

[51] Int. Cl.$^5$ .................... C07D 209/20; C07C 229/36
[52] U.S. Cl. .................... 548/497; 548/496; 562/443; 562/445
[58] Field of Search ................ 548/497; 562/443, 445

[56] References Cited

U.S. PATENT DOCUMENTS

| | | |
|---|---|---|
| 3,045,026 | 7/1962 | Eisenbraun . |
| 4,133,753 | 1/1979 | Takeuchi et al. .................... 562/443 |
| 4,769,474 | 9/1988 | Miyahara et al. .................... 548/497 |
| 4,910,336 | 3/1990 | Goodman . |
| 4,956,471 | 9/1990 | Ito et al. .............. 562/554 |
| 5,030,750 | 7/1991 | Kuzira et al. ....................... 562/554 |

FOREIGN PATENT DOCUMENTS

| | | |
|---|---|---|
| 0336818 | 10/1989 | European Pat. Off. . |
| 61-189266 | 8/1986 | Japan .................................... 548/497 |
| 1145512 | 3/1969 | United Kingdom . |

OTHER PUBLICATIONS

Gutsche et al., *Fundamentals of Organic Chemistry*, Prentice-Hall, Englewood Cliffs (1975) pp. 113–118.
Roberts et al., *Basic Principles of Organic Chemistry*, W. A. Benjamin (1964) pp. 1006–1007.
Dougherty et al., *J. Chromatog.*, vol. 42 pp. 415–416 (1969).

*Primary Examiner*—José G. Dees
*Assistant Examiner*—B. Frazier
*Attorney, Agent, or Firm*—Burns, Doane, Swecker & Mathis

[57]    ABSTRACT

A method is provided for the separation of at least one aromatic amino acid from an aqueous solution of mixed amino acids including the aromatic amino acid. The aqueous solution is brought into contact with a strongly acidic gel-type cation exchange resin which has been converted into a salt with an alkali metal or an alkaline earth metal, whereby the aromatic amino acid is selectively sorbed by the cation exchange resin. The aromatic amino acid thus sorbed can then be desorbed from the ion exchange resin, preferably with water.

8 Claims, No Drawings

SEPARATION METHOD OF AMINO ACIDS

This application is a continuation of application Ser. No. 07/612,478, filed Nov. 14, 1990 now abandoned.

BACKGROUND OF THE INVENTION a) Field of the Invention

The present invention relates to a method for separating at least one amino acid from an aqueous solution of mixed amino acids, which solution is produced, for example, in an amino acid production process such as a synthetic process, a fermentation process, an enzymatic process or a proteolytic process.

b) Description of the Related Art

As adsorption-dependent separation methods for amino acids, ion exchange methods have been known for many years. According to one example of these ion exchange methods, treatment of an aqueous solution of various amino acids with a strongly acidic ion exchange resin is effected by converting the resin into the free form, namely, the H form, causing the resin to adsorb the amino acids thereon and then eluting the amino acids with aqueous ammonia. This method makes use of the fact that an amino acid is an ampholyte, whereby the amino acids are once bonded to functional groups of the ion exchange resin. Accordingly, the pH of the solution of the amino acids is lowered to convert the amino acids into cations, followed by the treatment with the ion exchange resin. The amino acids adsorbed on the resin through ion bonding are then treated with aqueous ammonia as an eluent to raise the pH, so that the cations of the amino acids are subjected to ion exchange with ammonium ions and are hence eluted. Further, the ion exchange resin can be regenerated into the H form with a mineral acid such as hydrochloric acid or sulfuric acid and can then be employed again for the adsorption of amino acids For example, Japanese Patent Application Laid-Open No. 73050/1981 discloses a method in which one or more aromatic amino acids in an aqueous solution, an aqueous alcohol solution or an alcohol solution are purified using a strongly acidic ion exchange resin of the macroporous type. Even in this method, the ion exchange resin is converted into the H form and, after ionic adsorption of the amino acids, the amino acids are eluted with an aqueous ammonia solution.

Serious drawbacks of such ion exchange methods reside in the use of an acid as a pH-adjusting agent or a regenerating agent and also in the use of aqueous ammonia as an eluent. To practice the above ion exchange methods on an industrial scale, many accompanying problems therefore arise For example, the acid employed must eventually be neutralized and discharged as an effluent from the system. On the other hand, ammonia used as an eluent accompanies amino acids as target substances for the separation Removal of ammonia is therefore indispensable to isolate the amino acids. Further, to discharge the thus-removed ammonia out of the system, it is necessary not only to neutralize the same but also to eliminate by a certain method its nitrogen fraction which causes trouble from the standpoint of environmental protection.

SUMMARY OF THE INVENTION

An object of the present invention is to provide a method for efficiently separating one or more specific amino acids from a solution, in which the specific amino acids are contained along with impurities, without developing the above-described drawbacks of the conventional methods.

In one aspect of the present invention, there is thus provided a method for separating at least one aromatic amino acid from an aqueous solution of mixed amino acids including said at least one aromatic amino acid. The method comprises providing a strongly acidic gel-type cation exchange resin which has been converted into a salt with an alkali metal or an alkaline earth metal; and bringing said aqueous solution into contact with said cation exchange resin, whereby said at least one aromatic amino acid is selectively sorbed by said cation exchange resin.

According to the present invention, desorption of the amino acid thus sorbed can be conducted with purified water without relying upon an acid or an alkali. Salt-forming ions bonded to the ion exchange resin, such as sodium ions, remain bonded throughout the treatment so that they are not eluted. Accordingly, the resin can be used, as it is, for the next separation treatment.

In the light of the chemical and technical common knowledge of those skilled in the art, it is believed to be impossible to achieve selective ion exchange separation of an amino acid by treating a solution of mixed amino acids with an ion exchange resin which has been converted into an alkali metal salt or alkaline earth metal salt form. Therefore, the present invention can also be considered extremely surprising from this viewpoint.

DETAILED DESCRIPTION OF THE INVENTION

Exemplary amino acids to which the present invention can be applied include aromatic amino acids—such as tryptophan, phenylalanine and tyrosine, and their alkyl derivatives, hydroxyl derivatives, alkoxyl derivatives and acetylated derivatives—as well as substituted derivatives of these aromatic amino acids Their specific examples include phenylglycine; 4- hydroxy- and 4-methoxyphenylglycines; phenylalanine; 4-methyl-, 2,3-dimethyl-, 4-isopropyl-, 4-chloro-, 4-fluoro-, 2-bromo-, 4-nitro-, 4-amino-, 4-methoxy-, 4-acetoxy-, 3,4-methylene-, 3,4-dihydroxy, 2-hydroxy- and 4-mercapto-phenylalanines; tyrosine; thyroxine; thyronine; phenylserine; kynurenine; tryptophan; 2-methyl-, 5-methyl-, 2-hydroxy- and 5-hydroxy-tryptophans; furylalanine; thienylalanine; naphthylalanine; and pyridylalanine.

The solution to be treated in accordance with this invention contains, in a dissolved form, at least one of the above aromatic amino acids and their substituted derivatives. The solvent of the solution to be treated is water or an aqueous solvent Impurities other than amino acids, said impurities being generally mixed in during a production process of an amino acid such as a synthetic process, a fermentation process, an enzymatic process or a proteolytic process, do not provide problems in the process of the present invention.

Illustrative aliphatic amino acids which may be contained in a solution to be treated include glycine, alanine, valine, leucine, isoleucine, serine, threonine, proline, methionine, arginine, histidine, lysine, aspartic acid, and glutamic acid.

Sorption of these non-aromatic amino acids on a strongly acidic gel-type cation exchange resin converted into an alkali metal salt or alkaline earth metal salt type is far more difficult compared to aromatic amino acids. One or more aromatic amino acids which are contained along with non-aromatic amino acids and are to be separated can therefore be specifically sorbed and separated by the resin when treated in accordance with the present invention.

No particular limitation is imposed on the concentration range of each aromatic amino acid in a solution which can be treated successfully by applying the present invention, as long as the aromatic amino acid is dissolved therein. However, the concentration may range, for example, from 0.01% to 20%, preferably 0.05% to 10% for tryptophan; from 0.01% to 25%, preferably 0.05% to 15% for phenylalanine; and from 0.001% to 10%, preferably 0.005% to 5% for tyrosine No particular limitation is imposed on the concentration range of each coexisting aliphatic amino acid in a solution which can be treated successfully by applying the present invention, as long as the aliphatic amino acid is dissolved therein. However, the concentration may range, for example, from 0.01% to 80%, preferably 0.01% to 30%, more preferably 0.02% to 25%. It may be 0.01% to 50%, preferably 0.02% to 40% for serine; and from 0.01% to 25%, preferably 0.02% to 20% for alanine.

As the strongly acidic gel-type ion exchange resin in the present invention, a sulfonated product of a styrene-divinylbenzene copolymer is used. Exemplary cation exchange resins of this sort are commercially available under various trade names such as "Lewatit S100", "Lewatit S109", "Lewatit MDS1368" and "Lewatit TSW40" (products of Bayer AG); "DIAION SK1B" (product of Mitsubishi Chemical Industries, Ltd.); "Dowex HCR-S", "Dowex 50WX1" and "Dowex 50WX2" (products of Dow Chemical Company); and "Amberlite IR120" and "Amberlite IR122" (products of Rohm & Haas Company).

To use these cation exchange resins for the objects of the present invention, they must be in the form of an alkali metal salt or an alkaline earth metal salt. If they are not commercially available in such a form, it is necessary to convert an H-form ion exchange resin into such a salt form. As a salt-forming element, one or more metals selected from Li, Na, K, Rb, Cs, Be, Mg, Ca, Sr and Ba can be suitably employed. To convert an ion exchange resin into the form of such an alkali metal salt or alkaline earth metal salt, it is necessary, as known per se in the art, to bring an H-form ion exchange resin into contact with an aqueous solution of an alkali metal hydroxide such as sodium hydroxide or potassium hydroxide, an alkali metal halide, an alkali metal sulfate, an alkaline earth metal halide or an alkaline earth metal sulfate for the treatment of the former with the latter.

A description will next be made of an exemplary sorption operation in this invention, A column is packed with the above ion exchange resin which has been converted into an alkali metal salt or alkaline earth metal salt form. A solution to be treated, which contains an amino acid to be separated, is passed as an upflow or downflow through the packed layer, whereby the solution is brought into contact with the ion exchange resin and is treated with the same resin.

The pH of the solution to be treated is preferably 2-12, more preferably 4-11.

Although no particular limitation is imposed on the flow velocity of the solution upon passing it through the column, the flow velocity may generally be in the range of from 0.1 hr$^{-1}$ to 100 hr$^{-1}$, preferably from 0.3 hr$^{-1}$ to 60 hr$^{-1}$ in terms of space velocity.

To desorb the amino acid thus sorbed, the ion exchange resin with the amino acid sorbed thereby is brought into water which is substantially free of any acid or alkali. An organic solvent or a mixture of an organic solvent and water can also be used if desired.

No particular limitation is imposed on the operation temperature for practicing the above sorption and desorption. However, the operation may generally be conducted at a temperature of from 0° C. to 100° C. The operation temperature at the time of sorption may be same as or different from that at the time of desorption. Sorption at a relatively low temperature is however advantageous as it results in a higher sorption capacity. In addition, desorption at a higher temperature is advantageous because the amount of a desorbing solvent can be reduced.

As an advantageous feature of the method of this invention, it is to be noted that no special desorbing solvent is required in the above desorbing operation.

In addition, the salt-forming element such as an alkali metal is always fixed on the ion exchange resin. It is therefore another important feature of the present invention that the salt-forming element is practically undesorbed even while the ion exchange resin is in contact with the amino-acid-containing solution and during the desorbing operation. Gathering from such phenomena, the amino acid sorbed by the ion exchange resin in this invention appears to be fixed in the ion exchange resin by a sort of "occlusion" rather than the so-called "ion exchange". Its exact mechanism has however not been fully elucidated.

The method of this invention can also be practiced batchwise by using a tank-shaped vessel or the like instead of conducting the same in a continuous manner by using a column.

According to the method of the present invention, selective sorption of one or more target amino acid or acids is feasible without exposing the amino acid or acids to the same strongly acidic or strongly basic atmosphere as in the conventional ion exchange methods. Further, the target amino acid or acids can be efficiently separated without using any chemical reagent for pH adjustment and any acid, alkali or organic solvent as a desorbing agent, although this has not been achieved by the prior art. The method of the present invention is therefore suitable. The present invention has brought about a further advantage that the resin can be used, as it is, for the next separation treatment after completion of the desorbing operation.

The present invention will hereinafter be described in detail by the following examples, in which all designations of "%" are weight-basis concentrations in the corresponding solutions. Liquid chromatography was used for the analysis of the composition of each solution.

EXAMPLE 1

A column of 16.0 mm in diameter was packed with "Lewatit TSW40-Na", a strongly acidic cation exchange resin (product of Bayer AG), to 500 mm height. Warm water was then circulated through a jacket to maintain the column at 30° C.

As an amino acid solution which was a stock solution to be treated, was employed an aqueous solution (stock solution) having the following composition—tryptophan: 1.0%, serine: 1.0%, glycine: 1.0%, and indole: 0.1%.

Into the column, 400 ml of the stock solution were charged as a downflow at a flow velocity of 2 in terms of space velocity. Through an outlet of the column, 400 ml of a treated solution were obtained The treated solution had the following composition— tryptophan: 0.01% or less, serine: 0.98%, glycine: 0.99%, and indole: 0.1%.

Subsequent to the above sorbing operation, 400 ml of purified water as a desorbing solvent were charged as a downflow at a flow velocity of 2 in terms of space velocity, and 400 ml of a desorbed solution were obtained through the outlet of the column. The desorbed solution had the following composition—tryptophan: 0.95%, serine: 0.02%, glycine: 0.01%, and indole: 0.001% or less.

The recovery rate of tryptophan into the desorbed solution was 95%, whereas the exclusion rates of serine and glycine from the desorbed solution were 98% and 99%, respectively.

After the desorption with purified water, a similar sorption/desorption operation was conducted again using the resin as it was. Substantially the same separation results were obtained.

EXAMPLE 2

The procedures of Example 1 were repeated under the same conditions except for the replacement of the strongly acidic cation exchange resin by "Lewatit MDS1368-K" (product of Bayer AG). The following results were obtained.

|  | Concentrations in solution after treatment | Concentrations in solution after desorption |
| --- | --- | --- |
| Tryptophan | $\leq 0.01\%$ | 0.96% |
| Serine | 0.98% | $\leq 0.01\%$ |
| Glycine | 0.98% | $\leq 0.01\%$ |
| Indole | 0.1% | $\leq 0.001\%$ |

The recovery rate of tryptophan into the desorbed solution was 96%, whereas the exclusion rates of serine and glycine from the desorbed solution were both 98%.

After the desorption with purified water, a similar sorption/desorption operation was conducted again using the resin as it was. Substantially the same separation results were obtained.

EXAMPLE 3

Under the same column conditions as in Example 1, 400 ml of a solution containing 1.0% of phenylalanine and 0.05% of tyrosine were treated as a stock solution. Through the outlet of the column, 400 ml of an effluent were obtained. The concentrations of phenylalanine and tyrosine in the effluent were both 0.001% or less.

The recovery rates of phenylalanine and tyrosine into the desorbed solution were both 99%.

After the desorption with purified water, a similar sorption/desorption operation was conducted again using the resin as it was. Substantially the same separation results were obtained.

EXAMPLE 4

Following the procedures of Example 1 except for the replacement of the strongly acidic cation exchange resin by "Lewatit S100-Na" (product of Bayer AG), 400 ml of a solution containing 1.0% of N-acetyltryptophan were treated. Through the outlet of the column, 400 ml of an effluent were obtained. The concentration of N-acetyltryptophan in the effluent was 0.001% or less.

After the desorption with purified water, a similar sorption/desorption operation was conducted again using the resin as it was. Substantially the same separation results were obtained.

EXAMPLE 5

The procedures of Example 1 were repeated under the same conditions except for the replacement of the strongly acidic cation exchange resin by "Lewatit TSW40-Ca" (product of Bayer AG). The following results were obtained.

|  | Concentrations in solution after treatment | Concentrations in solution after desorption |
| --- | --- | --- |
| Tryptophan | $\leq 0.01\%$ | 0.96% |
| Serine | 0.98% | $\leq 0.01\%$ |
| Glycine | 0.98% | $\leq 0.01\%$ |

The recovery rate of tryptophan into the desorbed solution was 96%, whereas the exclusion rates of serine and glycine from the desorbed solution were both 98%.

EXAMPLE 6

The procedures of Example 1 were repeated under the same conditions except that a cation exchange resin obtained by converting "Lewatit S100-Na" (product of Bayer AG) into its Mg type was used in place of the strongly acidic cation exchange resin and an aqueous solution having the following composition—tryptophan, phenylalanine, alanine, serine and glycine: 1.0% each—was used as an amino acid solution to be treated. The preparation of the Mg type was conducted in the following manner. "Lewatit S100-Na" (200 ml) was packed in a column, and a 4% aqueous HCl solution in an amount as much as 10 times the amount of the resin was caused to flow down through the column so that the resin was converted into the H form. A 4% aqueous $MgCl_2$ solution in an amount as much as 10 times the amount of the resin was then caused to flow down through the column so that the resin was converted into the Mg-type. Thereafter, the resin was washed with 10 volumes of purified water.

The following results were obtained.

|  | Concentrations in solution after treatment | Concentrations in solution after desorption |
| --- | --- | --- |
| Tryptophan | 0.01% | 0.97% |
| Phenylalanine | 0.02% | 0.95% |
| Alanine | 0.96% | 0.021% |
| Serine | 0.98% | 0.01% |
| Glycine | 0.97% | 0.01% |

The recovery rates of tryptophan and phenylalanine into the desorbed solution were 97% and 95%, respectively, whereas the exclusion rate of alanine, serine and glycine from the desorbed solution were 96%, 98% and 97%, respectively.

What is claimed is:

1. A method for separating at least one aromatic amino acid having a benzene nucleus from an aqueous solution of mixed amino acids including said at least one aromatic amino acid, which comprises:
   providing a strongly acidic gel-type cation exchange resin which is a sulfonated product of a styrene-divinylbenzene copolymer and has been converted into a salt with an alkali metal or an alkaline earth metal; and bringing said aqueous solution into contact with said cation exchange resin, whereby said at least one aromatic amino acid is selectively sorbed by said cation exchange resin and wherein said sorbed amino acid is desorable with water.

2. The method of claim 1, further comprising desorbing said at least one aromatic amino acid from said cation exchange resin.

3. The method of claim 2, wherein said at least one amino acid is desorbed with water from said cation exchange resin.

4. The method of claim 1, wherein said solution contains at least one aliphatic amino acid.

5. The method of claim 1, wherein said cation exchange resin is packed in a column and is used as a packed layer.

6. The method of claim 1, wherein said cation exchange resin is in the form of a salt with an alkali metal selected from the group consisting of lithium, sodium, potassium, rubidium and cesium.

7. The method of claim 1, wherein said cation exchange resin is in the form of a salt with an alkaline earth metal selected from the group consisting of beryllium, magnesium, calcium, strontium and barium.

8. The method of claim 1, wherein said at least one aromatic amino acid is selected from the group consisting of tryptophan, phenylalanine and tyrosine.

* * * * *